United States Patent [19]

Schoemaker et al.

[11] Patent Number: 4,978,745
[45] Date of Patent: Dec. 18, 1990

[54] IMMUNOREACTIVE HETEROCHAIN ANTIBODIES

[75] Inventors: Hubert J. P. Schoemaker, Devon; Lee K. Sun, Media, both of Pa.

[73] Assignee: Centocor, Inc., Malvern, Pa.

[21] Appl. No.: 123,864

[22] Filed: Nov. 23, 1987

[51] Int. Cl.[5] ............................................. C07K 13/00
[52] U.S. Cl. ................................ 530/387; 435/240.2; 435/317.1; 435/69.1; 435/70.1; 435/240.26; 435/240.27
[58] Field of Search ..................... 435/68, 240.2, 320, 435/240.26, 240.27; 530/387

[56] References Cited

U.S. PATENT DOCUMENTS 4,474,893 10/1984 Reading .............................. 436/547
4,816,567 3/1989 Cabilly et al. ........................ 530/387

OTHER PUBLICATIONS

Cabilly et al., European Pat. Appl. Nov. 1984 A1 0125 023.
Boss et al., European Pat. Appl. Oct. 1984 A3 0120 694.
Sahagan et al., J. Immunology 137:1066-74 (1986).
Shadle et al., J. Cell Biol. 99:2056-60 (1984).
Morrison, Science 229:1202-1204 (1985).
Neuberger et al., published PCT application Mar. 1986 PCT/GB85/00392.
M. Shulman, et al., Nature, 276: 269-270 (1978).
T. Springer, et al., European Journal of Immunology, 8: 539-551 (1978).
L. K. Sun, et al., Proceedings of the National Academy of Science, U.S.A., 84: 214-218 (Jan. 1987).

Primary Examiner—Charles F. Warren
Assistant Examiner—Jasemine C. Chambers
Attorney, Agent, or Firm—Hamilton, Brook, Smith & Reynolds

[57] ABSTRACT

Immunoreactive heterochain antibodies are described. The heterochain antibodies are made up of light chain and heavy chain variable regions derived from different antibodies. The heterochain antibodies can exhibit antigen binding properties which are different from the parent antibodies from which they are derived. Methods of producing the heterochain antibodies and methods of their use in diagnostic and therapy are also disclosed.

6 Claims, 5 Drawing Sheets

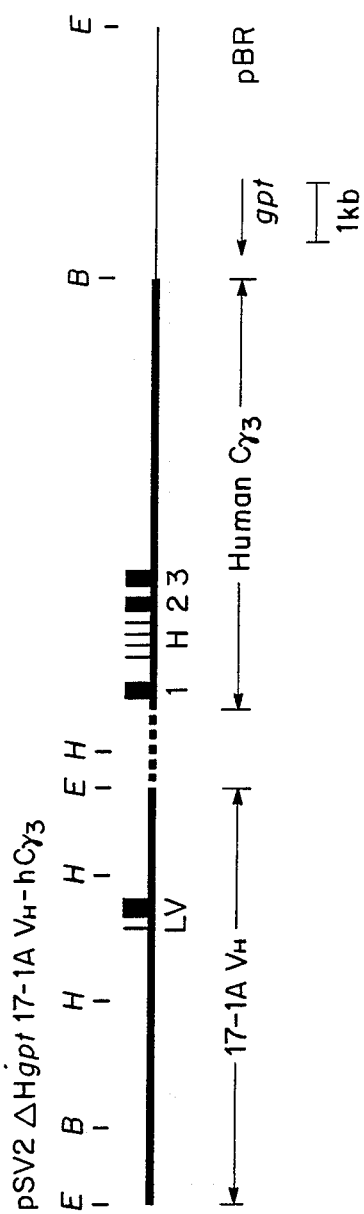
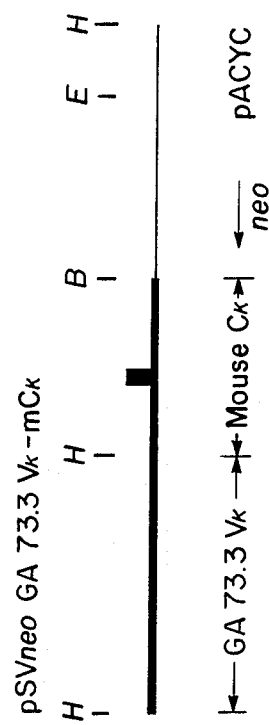
Fig. 1A
Fig. 1B

IMMUNOREACTIVE HETEROCHAIN ANTIBODIES

BACKGROUND

The introduction of hybridoma technology has revolutionized the biomedical field by allowing for the production of unlimited quantities of antibodies of a desired specificity (hereinafter monoclonal antibodies). In 1975, Kohler and Milstein (*Nature* 256:495 (1975)) disclosed that monoclonal antibodies could be produced by hybrid cell lines (hereinafter hybridomas) prepared by the fusion of spleen cells from an immunized animal with myeloma cells.

Monoclonal antibodies provide highly specific, well-characterized reagents. They have found wide applications in vitro for the identification, purification, and characterization of antigens. When the antigenic determinants recognized by the monoclonal antibodies are cell surface tumor-associated antigens, these reagents may also specifically accumulate at the tumor site. Increasingly they are being tested in vivo for tumor-imaging and therapy (Levy and Miller, Ann. Rev. Med. 34:107 (1983)).

In some cases, treatment With monoclonal antibodies alone has resulted in partial or complete regression of tumors. See papers in the proceeding of the Wistar Symposium on Immunodiagnosis and Immunotherapy with CO17-1A MAb in Gastrointestinal Cancer (*Hybridoma* 5:Suppl. 1 (1986)). Much effort has also been focused on modifications of monoclonal antibodies for immunodiagnostic and immunotherapeutic applications. For example, monoclonal antibodies can be used for targeted delivery of effective agents in the form of antibody-drug conjugates (Baldwin, in *Monoclonal antibody therapy of human cancer.* p. 23 (1985) or as bifunctional antibodies (Staerz and Bevan, PNAS 83:1453 (1986)).

SUMMARY OF THE INVENTION

This invention pertains to immunoreactive heterochain antibody (immunoglobulin). The heterochain antibody comprises at least one heavy chain variable region derived from a first antibody and at least one light chain variable region derived from a second antibody, the variable regions being associated to form a functional antigen binding site. The antigen binding site of the heterochain antibody is a composite of the variable regions of the antibodies from which the heterochains are derived and consequently can exhibit different binding properties (e.g. different affinity or specificity) than the parent antibodies. This invention also pertains to methods of preparing heterochain antibodies and to methods of diagnosis and therapy of disease employing the heterochain antibodies.

BRIEF DESCRIPTION OF THE FIGURES

FIG. 1 shows a restriction map of gene constructs for the production of heterochain antibodies (A) pSV2 ΔHgpt17-1AV$_H$-hC$\gamma$3 and (B) pSVneoGA73.3V$_\kappa$mC$_\kappa$.

DETAILED DESCRIPTION OF THE INVENTION

Figure 2:
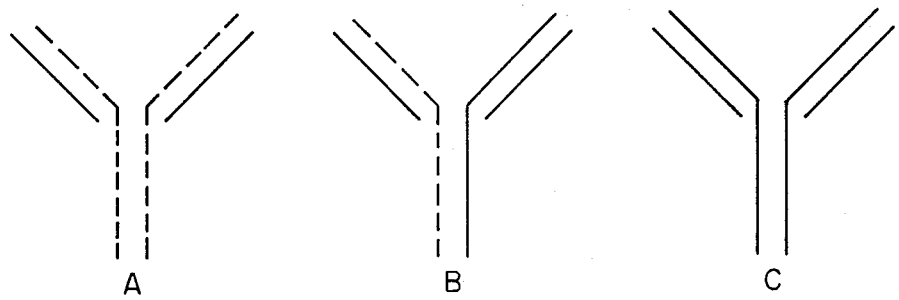
FIG. 2 shows a schematic illustration of the three types of IgG secreted by the HC1.1 cells. Solid lines represent the chimeric 17-1A heavy chain and broken lines represent Ig peptides of murine GA73.3 origin.

This invention pertains to immunoreactive heterochain antibodies and to methods of their preparation and use. The heterochain antibodies are made up of at least one light chain and at least one heavy chain derived from different antibodies. The heterochains are associated to form a functional antigen binding region. The combined chains form unique antigen binding region where one of the variable regions is derived from a first antibody and the other variable region is derived from a second antibody.

The heterochain antibodies of this invention can have different antigen or binding properties than the parent antibodies from which they are derived. For example, the antibodies can have different epitopic specificity or affinity than the parent antibody. In preferred embodiments the heterochain antibodies are derived from parent antibodies reactive with the same antigen or the same epitope (or related epitope). The invention provides a means for altering antibody binding characteristics to provide improved antibodies for specific applications in diagnosis and therapy.

The heterochain antibodies of this invention can be monovalent, divalent or polyvalent. Monovalent are dimers (HL) formed of a heavy chain from a first antibody associated through interchain disulfide bridges with a light chain from a second antibody. Divalent antibodies are tetramers (H$_2$L$_2$) formed of two associated dimers. Polyvalent antibodies can be produced, for example, by employing heavy chains which aggregate (e.g. heavy chains having mu type constant regions or aggregatable portions thereof).

The individual heterochains of the heterochain antibody can be chimeric chains where the variable region of the chain is derived from one animal species and the constant region of the chain is derived from a second animal species. For example, a murine/human chimeric chain can comprise a variable region derived from a murine antibody and a region derived from a human antibody. It is particularly advantageous to employ human constant regions to produce heterochain antibodies for in vivo use in humans because this reduces the risk of deleterious immune reactions in humans against the administered antibody. Further, human-derived constant regions are expected to have better effector function and longer circulating half-lives in humans.

The heterochains can also be truncated chains (truncated at the carboxyl end). For example, truncated heavy chains can be used to produce heterochain antibody fragments analogous to the antibody fragments Fv, Fab, Fab' or F(ab')$_2$ which are produced by enzyme cleavage. Heterochain antibodies having truncated chains are particularly useful for immunoscintigraphic procedures.

The heavy chains of the heterochain antibody can have constant regions selected from any of the five isotypes alpha, delta, epsilon, gamma or mu. In addition, heavy chains may be of various subclasses (such as the IgG subclasses). The different classes and subclasses of heavy chains provide for different antibody effector functions and, thus by choosing the desired heavy chain constant region, a heterochain antibody with a desired effector function can be produced. The light chains can have either a kappa or lambda constant chain.

Antibody heterochains for production can be derived from a variety of sources. Variable regions from antibodies against tumor-associated antigens can be combined to produce novel heterochain antibodies which have unique binding characteristics. Among the anti-tumor antibodies from which variable regions can be derived are antibodies specific for antigens associated with gastrointestinal (e.g. colon and pancreas), breast, ovarian, lung and renal cancer. Some specific examples of anti-tumor antibodies are 17-1A (gastrointestinal tumors), OC 125 (ovarian carcinoma), OV-TL3 (ovarian carcinoma), 103D2 (breast) and 123.C3 (renal carcinoma). Variable region may also be derived from antibody against an antigen associated with cardiovascular disease (such as anti-myosin antibody and antibody reactive with artherosclerotic plaques), antibody against infectious agents (such as antibody against bacterial toxins,(e.g. gram-negative lipopolysaccharide) and viral antigens) and antibody against components or a thrombrus (e.g. anti-fibrin antibody, anti-platelet antibody).

Heterochain antibodies of this invention can be made by several different methods. In one method, cells capable of producing a first antibody are transfected with nucleic acid (DNA or RNA) which encodes a heavy and/or light chain of a second antibody to yield transfected cell capable of expressing first and second antibody chains. The transfected cells are cloned and the resulting clones are selected for the ability to produce heterochain antibody. Suitable cells for transfection and production of heterochain antibody are lymphoid cells which are capable of producing a desired first antibody e.g., transfected B lymphocytes and hybridoma cells. Lymphoid cells which normally produce antibody possess the required cellular machinery for glycosylation and assembly of the heterochain antibodies.

In a preferred method of producing heterochain antibody, hybridoma cells which have lost the ability to produce one of the chains of the antibody which they normally produce (called chain-loss variants) are employed. In these cells, production of the normal homochain antibody is eliminated. The cells are transfected with DNA (or RNA) encoding a heterochain which replaces the light or heavy chain which the recipient cell has lost the capability to produce and which has the desired variable region. Transfected hybridomas are selected for production of the heterochain antibody. Hybridoma cells which are unable to produce an antibody chain can be selected by soft-agar cloning and screening with appropriate antiserum (Springer, et al. *Eur. J. Immunol.* 8:539 (1978)).

In another method for producing heterochain antibody, antibody-producing cells which have lost capability to produce both antibody chains are used. In this case, the nonproducing cell is transfected with nucleic acid (DNA or RNA) coding for both the heavy chain and the light chain of the heterochain antibody. Each encodes a variable region of a different antibody. Transfected cells are selected for products of the heterochain antibody. For this method, hybridoma or myeloma cells which are incapable of producing either antibody are available. An example is the non-producing myeloma cell line Sp2/O (Shulman et al., *Nature* 276:269 (1978)).

According to the methods of this invention appropriate recipient cells are transfected with nucleic acid constructs, preferably DNA, encoding the desired antibody heterochain or heterochains. In general, DNA constructs for each of the light and heavy chains components of the heterochain antibody comprise a fused gene comprising a first DNA segment which encodes at least the functional portion of the variable region linked to a second DNA segment encoding at least a part of a constant region. The fused gene is assembled in or inserted into a vector for transfection of the appropriate recipient cells.

In preferred embodiments the fused gene construct will comprise a functionally rearranged gene encoding a variable region for an antibody chain linked to a gene encoding a constant region of an antibody chain. The construct will also include the endogenous promoter and enhancer for the variable region encoding gene. For example, the variable region encoding genes can be obtained as a DNA fragment comprising the leader peptide, the VJ gene (functionally rearranged variable (V) regions with joining (J) segment) and the endogenous promoter and enhancer for these genes. This fragment is linked to a DNA fragment containing the gene encoding the desired constant region (or a truncated portion thereof).

Genes encoding antibody light and heavy chains can be obtained from lymphoid cells which produce the antibodies specific for the desired antigen or epitope. Many antibody producing cell lines are presently avaiable. For example, available hybridoma cell lines which produce antibody against tumor associated antigens (e.g. 17-1A, CA125 and others) provide a source of immunoglobulin variable region genes against tumor-associated antigens. Hybridoma cell lines producing antibody against a desired antigen can be made by standard procedures of Kohler and Milstein, e.g. challenging a rodent with a desired antigen, forming fused hybrid cells between antibody producing cells and a myeloma cloning the hybrid and selecting clones which produce antibody against the antigen. Techniques for production of hybridoma cells which produce antibody against tumor-associated antigens are also known in the art. See e.g., U.S. Pat. No. 4,172,124 Koprowski et al.

Constant regions can be obtained from antibody-producing cells by standard cloning techniques. Human constant regions are most preferred. Because genes representing the two classes of human light chains and the five classes of human heavy chains have been cloned, constant regions of human origin are readily available from these clones.

The fused genes encoding either the light or heavy chains are assembled into expression vectors which can be used to transfect a recipient cell. Suitable vectors for the heterochain gene constructs include plasmids of the types PBR322, PEMBL, and PUC. The introduction of the heterochain gene constructs into plasmid vectors to produce recombinant plasmids can be accomplished by standard procedures of eukaryotic cell transfection. In preferred embodiments, the vector contains two selectable genes-one for selection in a bacterial system and one for selection in a eukaryotic system. These vectors allow production and amplification of the fused genes in bacterial systems and subsequent transfection of eukaryotic cells and selection of transfected cells. Examples of selectable gene for the bacterial system are the genes which confer ampicillin resistance and the gene which confers chloramphenicol resistance. Two selectable genes for selection of eukaryotic transfectants are preferred: (i) the xanthine-guanine phosphoribosyltransferase gene (gpt), and (ii) the phosphotransferase gene from Tn5 (designated neo). Selection with gpt is based on the ability of the enzyme encoded by this gene to use xanthine as a substrate for purine nucleotide synthesis; the analogous endogenous enzyme cannot. In a medium containing xanthine and mycophenolic acid which blocks the conversion of inosine monophosphate to xanthine monophosphate, only cells expressing the gpt gene can survive. The product of the neo blocks the inhibition of protein synthesis in eukaryotic cells caused by the antibiotic G418 and other antibiotics of its class.

In methods where cells are to be cotransfected with genes encoding both the light and heavy chains of the heterochain antibody, the genes are preferably assembled in two different expression vectors which can be used to cotransfect a recipient cell. In this case, each vector contains a different selectable gene for eukaryotic transfectants. This allows cotransfection of the recipient cell and selection of cotransfected cells (i.e. cells that have received both vectors). Selection of cotransfected cells is accomplished by selection for both selectable markers, which can be done simultaneously or sequentially.

Several methods exist for transfecting lymphoid cells such as hybridoma and myeloma cells with vectors containing antibody chain encoding genes. A preferred way of introducing DNA into lymphoid cells is by electroporation. In the procedure recipient cells are subjected to an electric pulse in the presence of the DNA to be incorporated in to the cell. See e.g. Potter, et al. PNAS 81:7161 (1984). Another way to introduce DNA is by protoplast fusion. In this method, lysozyme is used to strip cell walls from bacteria harboring the recombinant plasmid containing the heterochain Ig gene to produce spheroplasts. The resulting spheroplasts are fused with the lymphoid cells in the presence of polyethylene glycol. After protoplast fusion, the transfectants are selected and isolated. (Oi, et al., *PNAS* 80:825 (1983)). Other techniques which can be used to introduce DNA into many cell types are calcium phosphate precipitation (Graham and van der Eb, *Virology* 52:456 (1973) and DEAE-dextran (Cullen, et al., *Nature* 307:241 (1984)).

The heterochain antibody genes can be expressed in nonlymphoid cells such as bacteria or yeast. When expressed in bacteria, the immunoglobulin heavy chains and light chains become part of inclusion bodies. Thus, the chains must be isolated and purified and then assembled into functional immunoglobulin molecules. The yield of heterochain antibody in bacteria may be low because bacteria lack the ability to glcosylate the expressed antibody chains.

The heterochain antibodies of this invention can be used in methods of diagnosis and therapy. The heterochain antibodies can be used in vitro in diagnostic tests such as immunoassay, as contrast agents (labeled heterochain antibodies) for in vivo imaging based upon a targeted antigen (e.g. immunoscintigraphy of tumor, myocardial infarct, artheroscelerotic plaque and thrombus), tumor therapy and prophylaxis and/or therapy of infectious diseases.

This invention is illustrated further by the following samples of the production of heterochain antibody HC1 containing chimeric (murine/human) 17-1A heavy chain and the murine GA73.3 light chain.

EXAMPLES

EXAMPLE 1

Transfection of chimeric 17-1A heavy chain gene into GA73.3 cells.

A. Construction of expression vector containing the chimeric 17-1A heavy chain gene: pSV2 ΔHgpt17-1AVH-hC$_{\gamma 3}$.

The functionally rearranged heavy chain variable gene of 17-1A was isolated and cloned into an expression vector containing a genomic DNA fragment encoding human $\gamma_3$ constant region to give pSV2Δ Hgpt17-1AVH-hC$_{\gamma 3}$ as described (Sun et al., *PNAS* 84:214 (1987)). The restriction map is shown in FIG. 1A. Transfection of myeloma cells with this gene construct, together with an expression vector containing the 17-1A chimeric light chain, resulted in the production of functional IgG that retained the specific binding to the surface antigen 17-1A expressed on human colorectal carcinoma SW1116 cells.

B. Transfection of pSV2 ΔHgpt17-1AVH-hC$_{\gamma 3}$ into GA73.3 cells.

DNA was transfected into GA73.3 cells by electroporation using Bio-Rad Gene Pulsar Transfection Apparatus. Approximately $8 \times 10^6$ cells in 0.8 ml of Dulbecco's phosphate-buffered saline (PBS) containing 30 μg of pSV2 ΔHgpt17-1AVH-hC$_{\gamma 3}$ were subjected to an electric field of 0.15 kV and a capacitance of 960 μFD at 4°. The cells were diluted with MEM medium supplemented with 15% FBS and plated out in a 96-well microtiter plate. After 48 hr, the medium was changed to MEM containing 0.5 μg/ml mycophenolic acid, 50 μg/ml xanthine, and 2.5 μg/ml hypoxanthine for selection of transfected cells.

C. Antibody production and purification.

Figure 3:
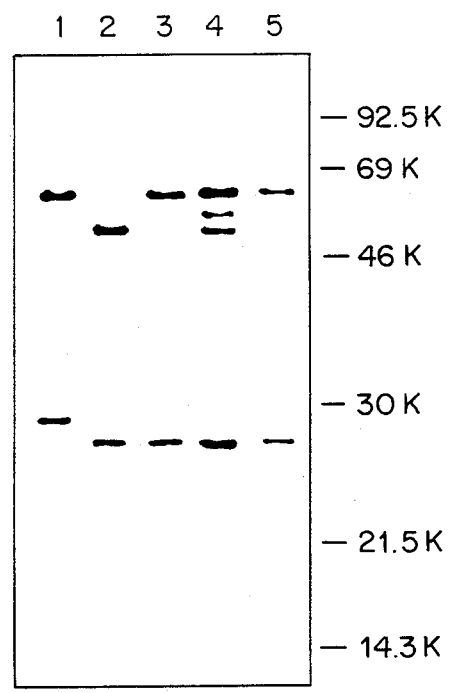
FIG. 3 shows SDS/polyacrylamide gel analysis of IgG produced by HC1.1 cells. Three μg of purified IgG was electrophoresed on a SDS/12% polyacrylamide gel under reducing conditions. Lane 1, chimeric 17-1A, G3K; lane 2, GA73.3; lane 3, HC1.2; HC1.1 before (lane 4) and after (lane 5) removal of GA73.3-derived heavy chain on Sepharose-bound anti-mouse IgG (Fc) antibody.

A stably transfected cell line HC1.1 was established and analyzed. The HC1.1 cells synthesized the mouse/human chimeric heavy chain in addition to the endogenous murine GA73.3 heavy and light chains. Since only the tetrameric antibody consisting of two heavy and two light chains can be secreted, there are three possible types of IgG in the culture supernatant, as illustrated in FIG. 2. Tissue culture supernatant was analyzed for IgG content by particle concentration fluorescence immunoassay using standard curves generated with purified human or mouse IgG. The assays were carried out with an automated instrument (Pandex Laboratories, Mundelein, Ill.). Concentration of IgG production was estimated to be 8 μg/ml by using polystyrene beads coated with goat anti-mouse IgG(Fc) antibody and fluorescein-conjugated goat anti-mouse IgG(Fc) antibody. This concentration represented the total amount of both IgG types B and C. When goat anti-human IgG(Fc) antibody coated polystyrene beads and its fluorescein conjugated probe were used in the assays with the same culture supernatant, the IgG content was estimated to be 1.2 μg/ml for IgG types A and B. IgG A and B were separated from C using an affinity column containing Sepharose-bound anti human IgG(Fc) antibody which specifically bound the human IgG(Fc) portion of IgG A and B. The eluate, when checked on reducing SDS/PAGE analysis, showed a homogenous light chain band and two heavy chain bands (FIG. 3), corresponding to the chimeric 17-1A heavy chain and the murine GA73.3 heavy chain. Mixture of A and B was then passed through a Sepharose-bound anti mouse IgG(Fc) antibody column to remove IgG B. The relative amounts of the chimeric to the murine heavy chains was about 100:1 after two column purifications as determined on Pandex using appropriate reagents. The resulting purified heterochain antibody, HC1.1, was used for HT29 cell binding assay.

D. Immunoactivity analysis of HC1.1 using human colorectal carcinoma HT29 cells.

Figure 4A:
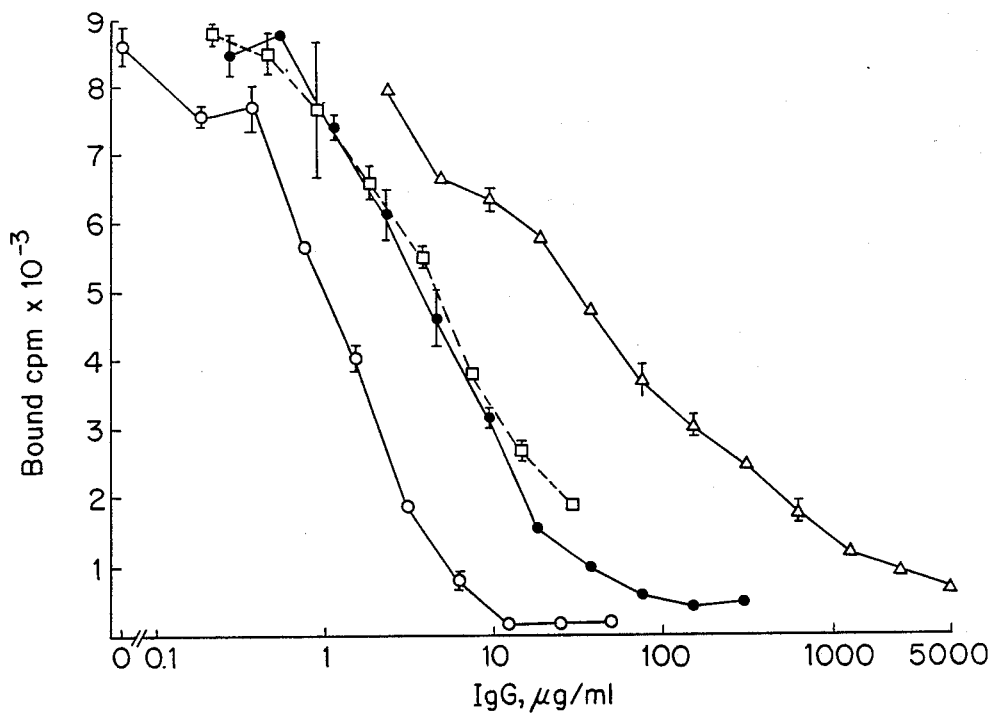
FIG. 4 shows the binding of iodinated monoclonal antibody (MAb) to HT29 cells in the presence of purified IgG of GA73.3 ( ), HC1.1 (☐ ☐), HC1.2 ( ), and 17-1A (Δ Δ). Iodinated MAb used is HC1.2 (A), GA73.3 (B), and 17-1A (C).

Sixty μg of purified IgG type A (HC1.2, see example 2) was labelled with Iodo-Beads (Pierce Chemical Company, Rockford, Ill.) using 1 mCi of $Na^{125}I$. After 10 min, the reaction was quenched with PBS containing 5% BSA. Free iodine was removed with a prepacked PD-10 column (Pharmacia). Specific activity was typically 10,000 cpm/ng of protein. Human colorectal carcinoma HT29 cell line was grown in MEM supplemented with 10% FBS. Cells were harvested with trypsin, washed, and resuspended in growth medium. Cells were then seeded in 96-well microtiter plates at $2 \times 10^5$ cells per well in 100 μl aliquots. After incubation at 37° for 17 hr, the cells were refed with 100 μl of cold medium, and kept at 4° for 0.5 hr. Each well was then incubated at 4° for 2 hr with medium containing 400,000 cpm of iodinated HC1.2 and different concentrations of cold competing IgG in a final volume of 100 μl. The cells were then washed 3 times with warm medium and cell-bound radioactivity was measured in a gamma-counter. Curves for binding of iodinated HC1.2 to HT29 cells as competed by different concentrations of purified IgG are shown in FIG. 4A. The concentrations required to inhibit 50% of the iodinated-HC1.2 binding (IC50) are estimated to be 1.3, 5.5, and 45 μg/ml for MAb GA73.3, HC1.1 and 17-1A, respectively. The results indicated that HC1.1 bound to the surface antigen of HT29 cells with different affinity or specificity when compared to MAb GA73.3 and 17-1A.

EXAMPLE 2

Transfection of chimeric 17-1A heavy chain gene into GA73.3L cells.

A. Use of a heavy chain-loss variant of GA73.3, GA73.3L.

In example 1, the transfection of a heavy chain gene into GA73.3 cells, and the two column-purification of the desired heterochain antibody (FIG. 2A) from the other possible IgG (FIG. 2B, 2C) present in the culture supernatant of the HC1.1 cells is described. To generate a cell line that produced only the heterochain antibody, we used GA73.3L as the recipient cell line for the heavy chain gene, pSV2 Δ Hgpt17-1AVH-hCγ3. GA73 3L is a heavy chain-loss variant that lost the ability to synthesize the heavy chain. Heavy chain-loss variant cell lines can be selected according to published protocols. GA73.3L, however, occurred naturally during continuous cell culture. GA73.3L cells ceased production of the heavy chain but retained the ability to synthesize the light chain in the cytoplasm. Upon transfection with pSV2 ΔHgpt17-1AVH-hCγ3, the GA73.3L cells secreted a monoclonal antibody containing the chimeric 17-1A heavy chain and the murine GA73.3 light chain.

B. Transfection of pSV2 Δ -H17-1AVH-hCγ3 into GA73.3L cells.

DNA was transfected into the GA73.3L cells by the method of electroporation as described in section B of example 1. Forty-eight hours after electroporation, cells were selected in growth medium (DMEM supplemented with 15% FBS) containing 0.5 μg/ml of mycophenolic acid, 50 μg/ml of xanthine, and 2.5 μg/ml of hypoxanthine.

C. Antibody production and purification.

A stably transfected cell line HC1.2 was established and analyzed. Tissue culture supernatant was analyzed for IgG content using the same method as described in section C of example 1. Concentration of IgG production was estimated to be 8 μg/ml by using polystyrene beads coated with goat anti-human IgG(Fc) antibody and fluorescein-conjugated goat anti-human IgG(Fc) antibody. Heterochain antibody HC1.2 was purified on an affinity column of Sepharose-bound goat anti-human IgG(Fc) antibody. The purified IgG showed two bands corresponding to the 17-1A chimeric heavy chain and the murine GA73.3 light chain on reducing SDS/PAGE analysis (FIG. 3), and therefore had a structure corresponding to FIG. 2A.

D. Immunoactivity analysis of MAb HC1.2 using HT29 cells.

Figure 4B:
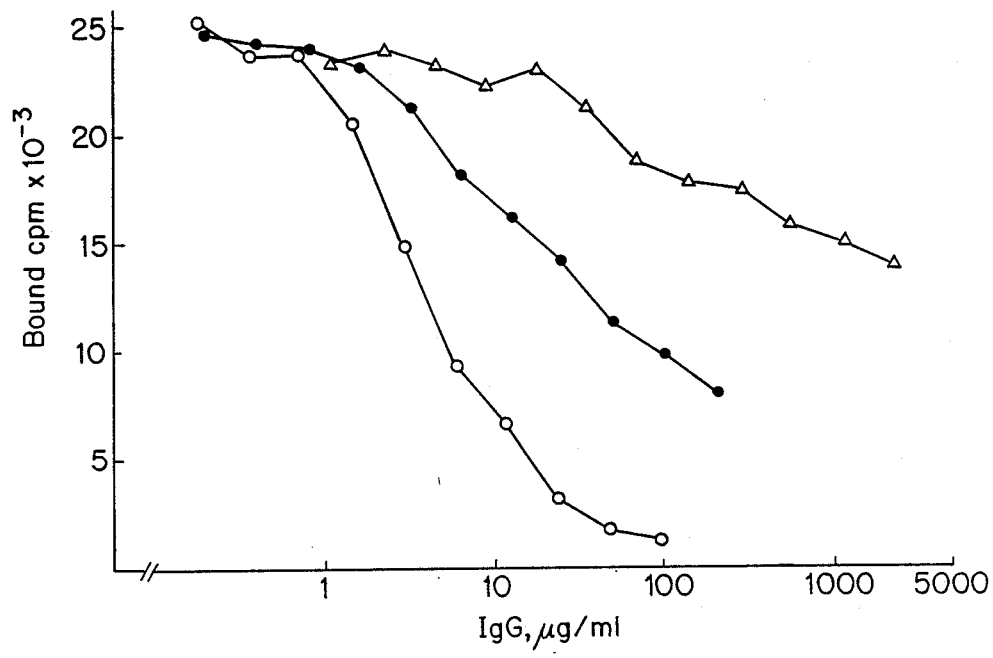
Figure 4C:
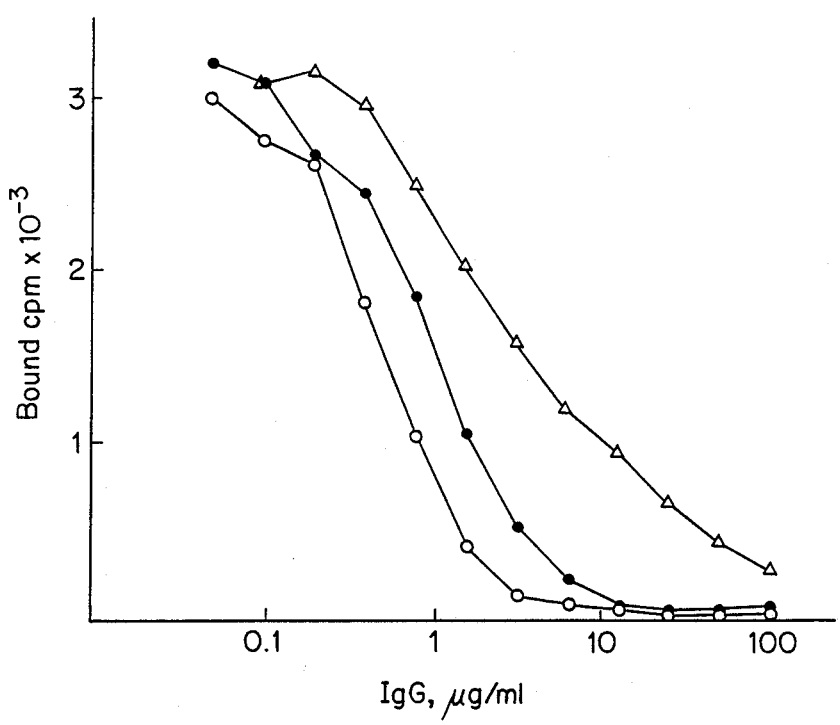

The cell binding assays were done according to section D of example 1. Curve for binding of iodinated HC1.2 to HT29 cells as competed by different concentrations of MAb HC1.2 is shown in FIG. 4A. The concentration required to inhibit 50% of the iodinated-HC1.2 is estimated to be 5.0 μg/ml. Competitive HT29 cell binding assays were also carried out using iodinated MAb GA73.3 (FIG. 4B) and MAb 17-1A (FIG. 4C). IC50 values were estimated from binding curves and summarized in Table 1. When iodinated GA73.3 was used, IC50 values of GA73.3, HC1.2, and 17-1A were 4.2, 42 and 4000 μg/ml, respectively. When iodinated 17-1A was used, IC50 values of GA73.3, HC1.2 and 17-1A were 0.45, 0.96 and 3.0 μg/ml, respectively. In each case, the IC50 values of HC1.2 were different than either of GA73.3 and 17-1A. The results indicated that MAb HC1.2 had different binding affinity than the two antibody from which its heavy and light chains were derived. It is also possible that the heterochain antibody recognized a different epitope of the surface antigen of HT29 cells.

TABLE 1

Summary of IC50 values (μg/ml) in competitive binding assays using HT29 cells.

| iodinated MAb | competing MAb | | | |
|---|---|---|---|---|
| | GA73.3 | HC1.1 | HC1.2 | 17-1A |
| A. HC1.2 | 1.3 | 5.5 | 5.0 | 45 |
| B. GA73.3 | 4.2 | N.D. | 42 | 4000 |
| C. 17-1A | 0.45 | N.D. | 0.96 | 3.0 |

EXAMPLE 3

An alternative method to produce a cell line that secrets the heterochain antibody HC1 is to transfect both the heavy and light chain genes into a mouse myeloma cell line. This approach requires the cloning of the functionally rearranged light chain variable region gene of the GA73.3 cells. The light chain variable gene is then cloned into expression vector containing the mouse κ constant region gene. Transfection of this light chain gene construct together with pSV2 ΔHgpt17-1AVH-hC$_{\gamma 3}$ into nonproducing mouse myeloma SP2/O cells allows selection of stable cell lines producing heterochain antibody consisting chimeric 17-1A heavy chain and GA73.3 light chain.

A. Cloning of the functionally rearranged light chain variable gene of GA73.3 and construction of the expression vector.

Figure 5:
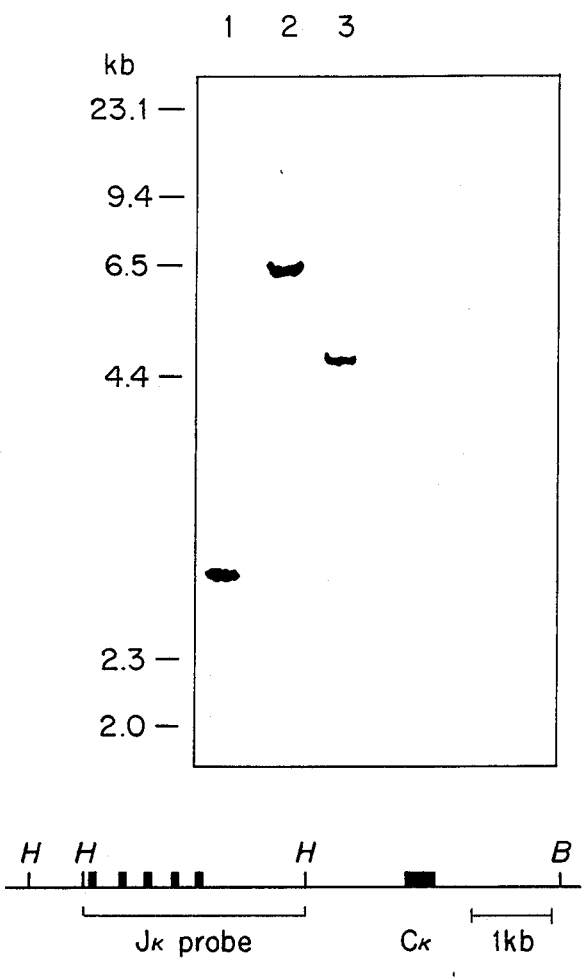
FIG. 5 shows a Southern blot analysis. Ten μg of genomic DNA was digested with HindIII, fractionated on a 0.7% agarose, and transferred to nitrocellulose. Bound DNA was hybridized with the mouse J$_\kappa$ probe. The 2.7 kb HindIII restriction fragment from the mouse germline J$_\kappa$ locus is shown below the autoradiogram. Lane 1, mouse liver DNA as a germline control; lane 2, 653, a mouse myeloma cell line; lane 3, GA73.3, a hybridoma cell line derived by using 653 as a fusion partner.

FIG. 5 shows the Southern analysis of rearranged fragments containing J$_\kappa$ sequences. DNA of GA73.3 cells gave a rearranged HindIII fragment of 4.6 kb which was different from the 6.5 kb band characteristic of the fusion partner, 653. This 4.6 kb HindIII DNA fragment thus contains the functional VJ rearrangement in the κ light chain locus of the GA73.3 cells. A partial genomic library can be constructed with enriched DNA fragments of appropriate sizes using phage vector such as Charon 27 or Lambda ZAP (Stratagene, San Diego, Calif.). Alternatively, a complete genomic library can be constructed using EMBL-3A phage vectors (Stratagene). The recombinant plaques of genomic libraries are screened with the mouse J$_\kappa$ probe using standard techniques (Maniatis, et al. *Molecular Cloning: A Laboratory Manual* p316 (1982)). The 4.6 kb HindIII fragment is then joined to the genomic DNA segment encoding mouse constant region in an expression vector containing a dominant selectable marker, neo. The restriction map of this light chain gene construct, pSVneoGA73.3V$_\kappa$-mC$_\kappa$, is shown in FIG. 1B.

B. Transfection of the heavy and light chain constructs into mouse myeloma Sp2/O cells. The heavy and light chain vectors shown in FIG. 1, pSV2 ΔHgpt17-1AVH-hC$_{\gamma 3}$ and pSVneo GA73.3V$_\kappa$-mC$_\kappa$, are used to transfect the nonproducing mouse myeloma Sp2/O cells. The heavy chain vector contains the gpt gene and the light chain vector contains the neo gene, it is therefore possible to select for cells that have integrated these two vectors by growing transfected cells in medium containing both mycophenolic acid and the antibiotic G418. Transfer of DNA into Sp2/O cells is carried out by electroporation as in section B of example 1. The optimal electric field is 0.2 kV for Sp2/O cells. Forty-eight hr after electroporation, the transfected cells are selected in growth medium (DMEM supplemented with 15% FBS) containing 1 μg/ml of mycophenolic acid, 50 μg/ml of xanthine, 2.5 μg/ml of hypoxanthine, and 1 mg/ml of G418. Stable transfected cell lines are established and analyzed.

C. Antibody characterization and purification, immunoactivity analysis are done according to section C and D of example 2.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An immunoreactive heterochain anti-17-1A antibody or antibody fragment, comprising at least one heavy chain variable region derived from a first antibody and at least one light chain variable region derived from a second antibody, wherein the chain regions are associated to form a functional antigen binding site, such that the binding affinity differs from that of either parental antibody and the first and second antibodies are specific for a 17-1A antigen or epitope.

2. An immunoreactive heterochain anti-17-1A antibody comprising at least one heavy chain derived from a first antibody and at least one light chain derived from a second antibody, wherein the chains are associated to form a functional antigen binding region, such that the binding affinity differs from that of either parental antibody and the first and second antibodies are specific for a 17-1A antigen or epitope.

3. An immunoreactive heterochain antibody of claim 2, wherein the heavy chain has a truncated constant region.

4. An immunoreactive heterochain antibody of claim 2, which is a bivalent tetramer.

5. An isolated immunoreactive heterochain antibody produced by the cell line HC1.1.

6. An isolated immunoreactive heterochain antibody produced by the cell line HC1.2.

* * * * *